(12) United States Patent
Bartels et al.

(10) Patent No.: US 8,862,246 B2
(45) Date of Patent: Oct. 14, 2014

(54) IMPLANTABLE DEVICE

(75) Inventors: Klaus Bartels, Berlin (DE); Heinrich Buessing, Berlin (DE); Timo Frenzel, Berlin (DE); Gernot Kolberg, Berlin (DE); Michelle Maxfield, Berlin (DE); Ingo Weiss, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 403 days.

(21) Appl. No.: 13/301,666

(22) Filed: Nov. 21, 2011

(65) Prior Publication Data
US 2012/0157811 A1 Jun. 21, 2012

Related U.S. Application Data

(60) Provisional application No. 61/424,074, filed on Dec. 17, 2010.

(51) Int. Cl.
*A61N 1/08* (2006.01)
*A61N 1/05* (2006.01)

(52) U.S. Cl.
CPC .......... *A61N 1/0563* (2013.01); *A61N 2001/086* (2013.01)
USPC ............................ 607/148; 600/374; 607/115

(58) Field of Classification Search
CPC .......................... A61N 1/3718; A61N 1/37223
USPC ....................................................... 607/148
See application file for complete search history.

(56) References Cited

U.S. PATENT DOCUMENTS

| | | | |
|---|---|---|---|
| 2005/0222647 A1* | 10/2005 | Wahlstrand et al. | 607/72 |
| 2007/0088416 A1* | 4/2007 | Atalar et al. | 607/115 |
| 2007/0255377 A1 | 11/2007 | Marshall et al. | |
| 2009/0149920 A1 | 6/2009 | Li et al. | |
| 2010/0160997 A1* | 6/2010 | Johnson et al. | 607/45 |
| 2010/0318164 A1 | 12/2010 | Chen et al. | |
| 2010/0324639 A1* | 12/2010 | Stevenson et al. | 607/116 |

FOREIGN PATENT DOCUMENTS

WO 2010/078552 7/2010

OTHER PUBLICATIONS

European Search Report dated Feb. 27, 2013, 5 pages.

* cited by examiner

*Primary Examiner* — Christopher D Koharski
*Assistant Examiner* — Natasha Patel
(74) *Attorney, Agent, or Firm* — ARC IP Law, PC; Joseph J. Mayo

(57) ABSTRACT

Temporarily or permanently implantable medical device, having at least one longitudinally extended first electrical conductor having a functional lead, which is connected to a functional electrode pole for dispensing therapeutic signals or for detecting diagnostic signals, and including at least one second electrical conductor, which is coupled to the functional lead and is guided with it in a shared insulating sheathing, such that a coupling between the functional lead and the second electrical conductor is designed to input electromagnetic radiofrequency waves guided in the functional lead at least partially into the second electrical conductor.

16 Claims, 5 Drawing Sheets

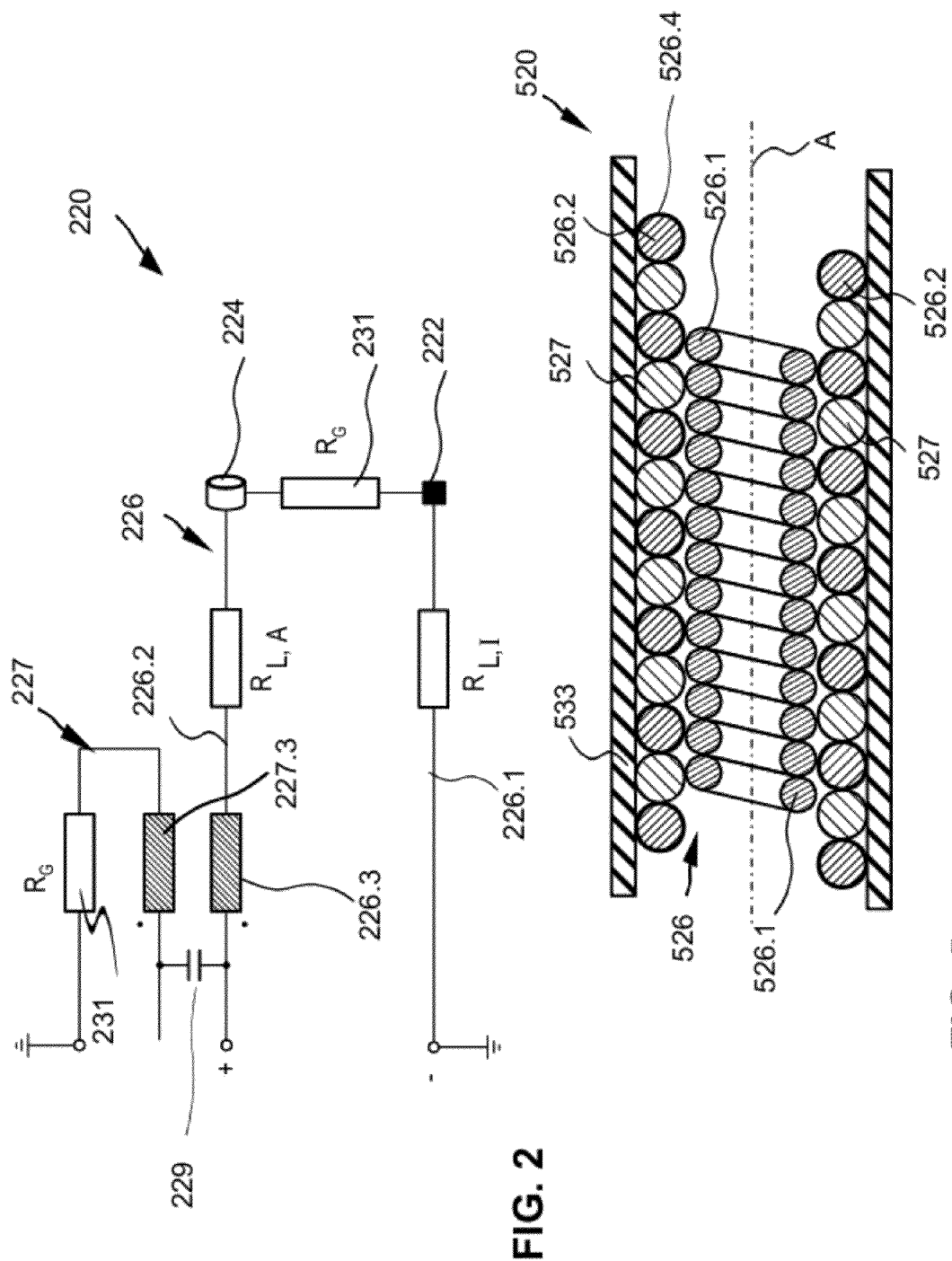

IMPLANTABLE DEVICE

This application claims the benefit of U.S. Provisional Patent Application 61/424,074 filed on 17 Dec. 2010, the specification of which is hereby incorporated herein by reference.

BACKGROUND OF THE INVENTION

1. Field of the Invention

At least one embodiment of the invention relates to a permanently or temporarily implantable device having an longitudinally extended electrical conductor.

2. Description of the Related Art

Such devices, for example, electrode leads for electrostimulation, have the disadvantage that the electrical conductors thereof can heat up in an MRI machine because the alternating magnetic fields prevailing in the MRI machine induce substantial electrical currents in the electrical conductor. For this reason, heart pacemaker patients today usually cannot be examined in an MRI machine or can be examined only to a limited extent.

Implantable heart pacemakers or defibrillators typically have at least one stimulation electrode lead, wherein said electrode lead has a standardized electrical connection on its proximal end, said end being provided for connection to the heart pacemaker or defibrillator, and said electrode lead has one or more electrode poles on its distal end, said distal end being provided for placement in the heart. Such an electrode pole serves to deliver electrical pulses to the (myocardial) tissue of the heart or for sensing electrical fields to be able to sense an activity of a heart as part of so-called sensing. Electrode poles are typically provided in the form of a ring around the electrode lead, having an electrically conductive surface or in the form of a point electrode or tip electrode on the distal end of the electrode lead. The electrode poles are electrically connected to contacts of the electrical connection of the electrode lead at the proximal end thereof by way of one or more electrical conductors. The electrode leads on their proximal end and the electrode poles on the distal end of the electrode lead run between the contacts of the electrical connection, these electrical conductors electrically connecting one or more of the electrode poles to one or more of the contacts. These electrical conductors may be used to transmit stimulation pulses to the electrode poles and also to transmit electrical signals picked up by the electrode poles to the proximal end of the electrode lead. In the following description, these electrical conductors are referred to as functional leads in the course of the following description. Such functional leads are electrical conductors, which are necessary for the functions of the respective electrode lead and as such are exposed to the risk that electrical currents may be induced in them by external alternating magnetic fields, but these electrical currents may result in unwanted heating of the functional leads or of the electrode poles connected to them, for example.

BRIEF SUMMARY OF THE INVENTION

The problem addressed by the at least one embodiment of the invention is to create a medical device which solves the problem described above.

This problem is solved according to at least one embodiment of the invention by a temporarily or permanently implantable medical device, comprising
at least one longitudinally extended first electrical conductor having a functional lead, which is connected to a functional electrode pole, for delivering therapeutic signals or for detecting diagnostic signals, and comprising
at least one second electrical conductor, which is coupled to the first electrical conductor and is guided in a shared insulating sheathing, such that a coupling is formed between the first and the second electrical conductors, electromagnetic radiofrequency waves are guided in the first conductor and are input at least partially into the second electrical conductor.

The functional lead may be designed to be either coaxial, having an internal conductor and an external conductor, or as a cord.

In the case of a coaxial design, this object is achieved by a temporarily or permanently implantable medical device, comprising
at least one longitudinally extended first electrical conductor having a functional lead, an internal conductor and an external conductor and connected to a functional electrode pole for delivering therapeutic signals or for detecting diagnostic signals, and comprising
at least one second electrical conductor, which is coupled to the first electrical conductor and is guided in a shared insulated sheathing, such that coupling between the first and the second electrical conductors is designed to input electromagnetic radiofrequency waves guided in the first conductor at least partially into the second electrical conductor.

The medical device according to at least one embodiment of the invention achieves a reduction in the unwanted heating of the functional leads or the electrode poles, which are connected to them, said heating being caused by electrical currents, which can be induced in the functional lead of the electrical conductor by external alternating magnetic fields. In this way, an unwanted heating of the bodily tissue in the implanted state can be reduced, shifted at least partially to other areas of tissue or even prevented entirely. This is accomplished according to at least one embodiment of invention with the aid of the second electrical conductor, which is also referred to within the scope of this patent application as an additional lead, and with the aid of a coupling between the first and the second electrical conductors which are designed to input electromagnetic radiofrequency waves guided in the first conductor at least partially into the second electrical conductor.

Embodiments of the medical device according to at least one embodiment of invention are explained below. The additional features of the individual embodiments may be combined with one another to form additional embodiments of the medical device inasmuch as they are not described explicitly as mutually exclusive alternatives.

In preferred embodiments, the longitudinally extended electrical conductor is a temporarily or permanently implantable electrode lead for connecting one or more functional electrode poles to a control unit, for example, the control unit of an implantable cardiac pacemaker or an implantable defibrillator. However, the longitudinally extended conductor forms a medical device as such within the sense of the present description.

The coupling between the functional lead and the second electrical conductor (additional lead) may assume different forms. In one embodiment, it is an inductive coupling, in another embodiment, it is a capacitive coupling, and in a third embodiment it is an ohmic coupling. A combination of two or more of the aforementioned forms of coupling may also be utilized. Of the various forms of coupling mentioned, the design of the coupling which is strongest in the range of the electromagnetic radiofrequency waves in a comparison of the various implementation possibilities is preferred. In this way, the heating of the bodily tissue surrounding the electrical conductor due to induced high-frequency electrical currents can be reduced to the greatest extent.

In one embodiment, the coupling is provided at only one location in the longitudinal extent of the functional lead. In one variant, a plurality of coupling sites is present along the longitudinal extent of the functional lead. The same coupling form may be used at all the coupling sites. Alternatively, different coupling forms are used at different coupling sites.

Two or more additional leads may be coupled to the functional lead in the medical device. In one embodiment, the functional lead is coupled to a plurality of additional leads between its proximal end and the functional electrode pole over its longitudinal extent. This means that the functional lead is coupled to each of the respective additional leads via an individual coupling. This may be embodied in such a way that the functional lead and the respective additional lead are connected to one another in one of the respective parallel circuits that are connected in series with one another. However, it may also be embodied in such a way that there are two additional leads, for example.

This embodiment may be improved upon in a variety of ways. In one variant of this embodiment, of the additional leads, at least one second additional lead has a longitudinal extent corresponding at least approximately to the length of the functional lead. In another variant, the additional leads are each formed by a short conductor section, so that a plurality of short conductor sections may be used as the respective additional lead, each being individually coupled to the functional lead. These short conductor sections thus each have a much smaller longitudinal extent than the functional lead itself. They are preferably designed so that they achieve the strongest possible coupling to the functional lead over their longitudinal extent.

In alternative further embodiments of this embodiment, the various additional leads are either coupled to one another or uncoupled from one another. The coupling of the additional leads may in the first case be capacitive, inductive or resistive, or it may have a combination of at least two of the three aforementioned coupling forms. An example of a resistive coupling of additional leads to one another provides for an electrical series connection of at least two of the short additional leads. Such a coupling, for example, in the case of two additional leads, is provided at several locations in the shared longitudinal extent of the additional lead in one embodiment.

Alternatively, multiple additional leads are each coupled in parallel to the functional lead.

With regard to the number of additional leads, coupled to one another or uncoupled, there is a possible selection, depending on the needs of the respective application.

In one embodiment, the additional lead or at least one of the plurality of additional leads is additionally coupled to the functional electrode pole or a second functional electrode pole, which is different therefrom.

Coupling to one second functional lead of the electrical conductor and/or a second functional electrode pole is reasonable in order to additionally protect such a second functional lead or a second functional electrode pole connected to it from unwanted heating with the aid of one and the same additional lead.

In alternative embodiments, the additional lead is uninsulated, partially insulated or insulated. The additional lead is preferably designed so that it is optimally coupled to the bodily tissue with respect to the energy transfer to the bodily tissue. In one embodiment, at least one second electrode pole, which is different in its function from a functional electrode pole, is connected to the additional lead. The second electrode pole, which may also be referred to as a sacrificial electrode pole, thus does not have any diagnostic or therapeutic function but instead in the implanted state serves to input energy into the surrounding bodily tissue in at least one location, which is different from the functional electrode pole, thereby relieving the functional electrode pole and/or the functional lead.

In such an embodiment, the additional lead may be electrically insulated with respect to the tissue, for example, by a dielectric layer on the conductor material in the area of the functional electrode pole or the second electrode pole. In this way, in the implanted state a galvanic coupling to the surrounding bodily tissue is prevented but a capacitive or inductive coupling is made possible.

In such an embodiment, however, a galvanic coupling of the additional lead to the functional lead is preferably provided in at least one longitudinal section, which is different from the electrode pole. Such a galvanic coupling may be arranged in particular so that it is distributed in various locations over the shared longitudinal extent of the functional lead and the additional lead. This may be accomplished, for example, with the help of a plurality of galvanic loop contacts, which are distributed over the shared longitudinal extent. However, the galvanic coupling preferably allows a mechanical mobility of the functional leads and additional leads in relation to one another. A preferred embodiment accomplishes this with the help of one or more loop contacts. To improve the coupling without restricting the mobility, the additional lead may have conductive whiskers.

If a plurality of functional leads is coupled to one or more respective additional leads in the embodiment described above, which provides for galvanic coupling between the functional lead and the additional lead, then the noninsulating sections of different additional leads should be secured against a mutual short circuit, that is, they should not be allowed to come into mutual contact with one another.

In one embodiment, the additional lead is in the form of a hollow coil surrounding the internal conductor of the functional lead. It may be coiled coaxially about the first conductor, for example. Alternatively, the functional lead surrounds the additional lead, for example, likewise in a coaxial winding. Another alternative is a co-radial arrangement of functional leads and additional leads, in which an external conductor of the functional lead and of the additional lead in one variant wind around an internal conductor of the functional lead on a shared imaginary cylindrical lateral surface, such that the outer conductor of the functional lead is electrically insulated from the additional lead. In an alternative variant, an external conductor of the functional lead is wound in a coil around the additional lead and an internal conductor of the functional lead, such that the internal conductor and the additional lead are each guided in a hollow conical pattern in an imaginary shared cylindrical lateral surface, and the outside conductor is electrically insulated from the second electrical conductor.

In addition to the embodiments described herein other alternative embodiments may include some or all of the disclosed features.

BRIEF DESCRIPTION OF THE DRAWINGS

Additional embodiments of the medical device are explained below on the basis of the figures. They show:

FIG. 2 an equivalent circuit diagram of an embodiment of an electrode lead in which an inductive coupling is implemented between a functional lead and an additional lead;

FIG. 5 shows a schematic longitudinal sectional view of an electrode lead in which a galvanic coupling between a functional lead and an additional lead is implemented via loop contacts;

DETAILED DESCRIPTION OF THE INVENTION

Figure 1:
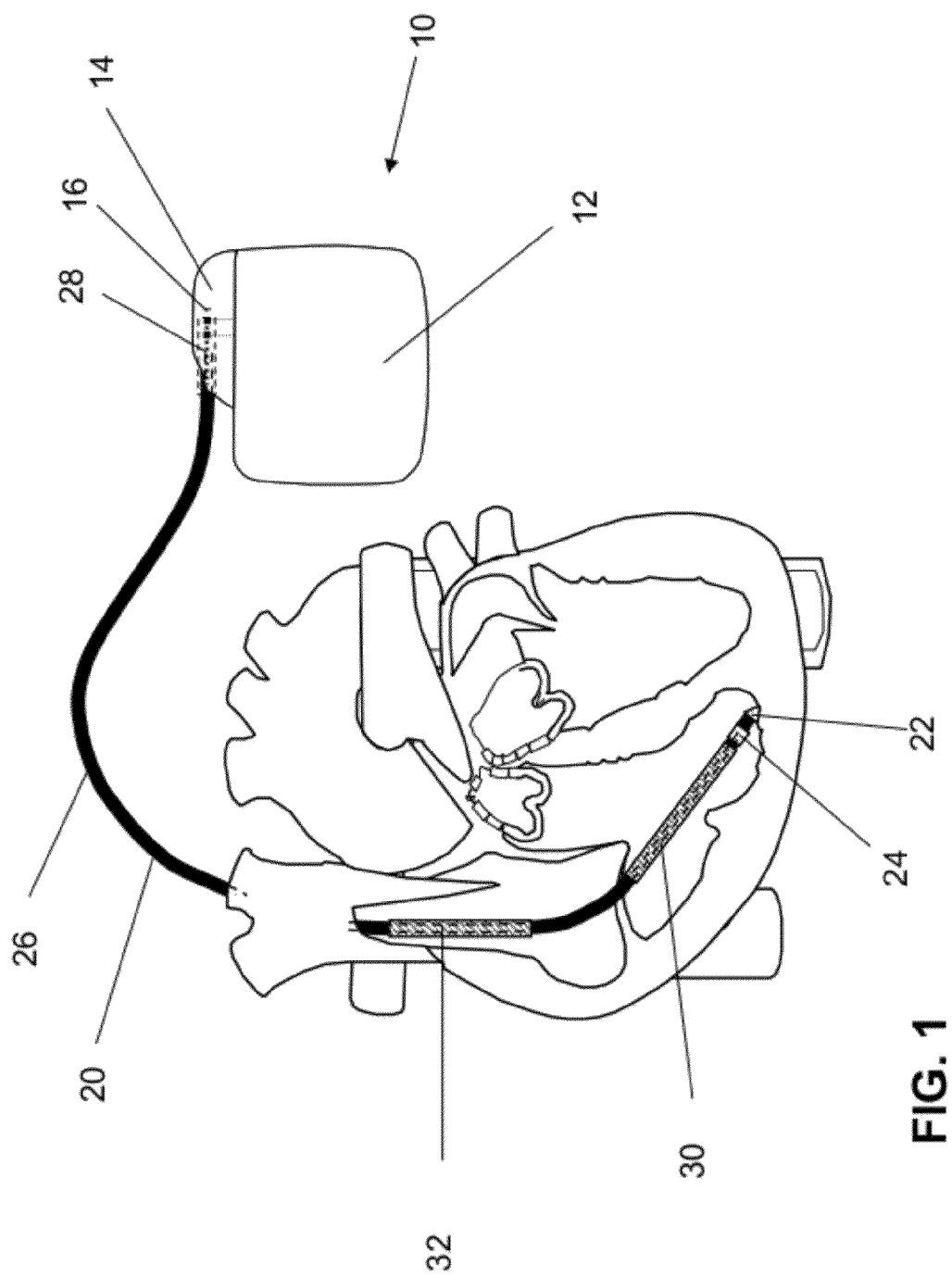
FIG. 1 embodiments of medical devices in the form of a heart pacemaker and an electrode lead connected thereto.

FIG. 1 shows, as examples of implantable medical devices, an implantable heart stimulator 10 and an implantable electrode lead 20 connected thereto.

The implantable heart stimulator 10 may be a heart pacemaker or a cardioverter/defibrillator (ICD). In the embodiment illustrated here, the heart stimulator 10 is a dual-chamber heart pacemaker for stimulation of the right atrium and the right ventricular or biventricular heart pacemakers which can also stimulate the left ventricle in addition to the right ventricle.

Such stimulators typically have a housing 12, which is usually made of metal and is consequently electrically conducting and may serve as a large-surface-area electrode pole. Typically a connection housing 14, which is also referred to as a "header," is attached to the outside of the housing 12. Such a header typically has contact connectors as receptacles for plug contacts. The contact connectors have electrical contacts 16, which are connected via appropriate leads to the electronics arranged inside the housing 12 of the heart stimulator.

The electrode lead 20 likewise constitutes an implantable medical device in the sense of this invention. Electrode poles in the form of a point electrode or tip electrode 22 as well as one ring electrode 24 arranged near the former are arranged on the distal end of the electrode lead in a conventional manner. The electrode poles 22 and 24 are designed in such a way that they serve to sense electrical potentials of the (myocardial) heart tissue or they serve to discharge electrical signals, for example, to dispense stimulation pulses to the heart tissue surrounding the electrodes, according to the function of the heart stimulator to which the electrode lead 20 is attached.

FIG. 1 shows how the electrode poles, that is, the tip electrode 22 and the ring electrode 24 and in certain cases the electrode lead 20 are located in the apex of a right ventricle of a heart.

Both the tip electrode 22 and the ring electrode 24 are electrically connected to a plug contact 28 at the proximal end of the electrode lead 20 via at least one electrical conductor 26 each. The plug contact 28 has electrical contacts, which correspond to the electrical contacts 16 of the contact connector in the connection housing 14 of the implantable heart stimulator.

As described in greater detail below, the electrical conductors 26 in the electrode lead 20 may be constructed in different longitudinal sections as primarily extended feed cables or as helical coiled leads. Such leads which electrically connect the functional electrode poles to electrical contacts of the plug contact on the proximal end of the electrode lead 20 are also characterized as functional leads in the scope of this description because they transmit therapeutic electrical signals from the plug contact to one or both electrode poles, or they convey sensed electrical potentials to the plug contact, these potentials representing signals from one or both electrode poles. Consequently, said leads serve to fulfill the elementary function of the medical device.

The electrical functional leads 26, which connect the electrode poles 22 and/or 24 to the electrical contacts of the plug 28 of the electrode lead 20, are surrounded over most of their length by an insulating sleeve, so that electrical contact is established with the tissue of the heart via the electrode poles in a targeted manner.

In addition to the electrode poles 22 and 24, which typically serve to stimulate the heart tissue (ventricular tissue in this case), the electrode lead 20 also has two additional large-surface-area electrode poles 30 and 32, which function as defibrillation electrodes and are formed by at least one uninsulated helical coiled wire.

It should be pointed out that the invention is explicated using this embodiment on the basis of a right ventricular pacemaker and defibrillator. However, in principle, an ablation electrode lead could also be cited as an example of a medical device in the sense of the invention, said ablation electrode lead likewise projecting into the heart of a patient and being controlled by a device outside of the patient's body and, for that purpose, connected to same. Furthermore, such electrode leads may also function in other applications upon technical adjustment for the special requirements of other specific uses to stimulate tissue or to relay signals to/from nerves, the brain and other organs, or as feeds from implantable sensors.

Different embodiments of the electrode lead 26 are described below on the basis of equivalent circuit diagrams in FIGS. 2 through 4. It should be pointed out that reference numerals, which should illustrate the relationship between the structural elements of an electrode lead shown there and the embodiment of FIG. 1, are used in FIGS. 2 through 5. The last two digits of a structural element represented in FIG. 1 also contain the reference notation used in FIG. 1. However, this implies only a functional correspondence and, unless otherwise indicated, should not mean that these are identical structural elements.

FIG. 2 shows an equivalent circuit diagram of an embodiment of an electrode lead 220 in which an inductive coupling has been implemented between a functional lead 226 and an additional lead 227, shown in the implanted state.

A functional lead 226 has an internal conductor 226.1 and an external conductor 226.2, which are connected proximally to a power supply of a control unit, which has been reduced to its function as a voltage source in this equivalent circuit diagram for the sake of simplicity. The internal conductor 226.1 is connected distally to a tip electrode pole 222. The external conductor 226.2 is connected to a ring electrode pole 224. Both electrode poles 222 and 224 are connected via a bodily tissue, represented by an ohmic tissue resistance 231.

An additional lead 227 which is also referred to as a second electrical conductor as part of this description, is inductively and capacitively coupled to the external conductor 226.1. An inductive coupling 226.3, 227.3 is achieved by means of a helical winding of the two coupled conductors, but preferably not necessarily in the same direction, i.e., of the external conductor 226.2 and of the additional lead 227, which thereby form the coupled inductors 226.3 and 227.3, which are coupled in the equivalent circuit diagram of FIG. 2. An additional capacitive coupling 229 of the two conductors 226.2 and 227 is obtained by running the two conductors 226.2 and 227 co-radially side by side and insulating them electrically from one another. Capacitance 229 may be influenced by the distance of the two conductors 226.2 and 227 from one another in their shared winding and/or due to the choice of the relative permittivity of the insulator between them.

The additional lead 227 is connected to the bodily tissue 231 via an additional electrode pole (not shown here), so that energy fed into the additional lead 227 via the inductive and capacitive coupling can be dispensed into the bodily tissue.

The unwanted heating of functional lead 226 or the electrode poles 222 and 224 connected thereto, caused by electrical currents which may be induced in the functional lead of the electrode lead by strong external alternating magnetic fields, such as those generated by an MRI machine, for example, is reduced with this electrode lead. In this way, an unwanted heating of bodily tissues in the area of the electrodes 222 and 224 in the implanted state can be reduced and at least partially displaced to other tissue areas or even prevented entirely.

This is accomplished with the aid of the additional lead 227 and with the aid of the coupling described here between the functional lead and the additional lead, which is designed to input electromagnetic radiofrequency waves guided in the first conductor at least partially into the second electrical conductor.

Figures 3, 4:
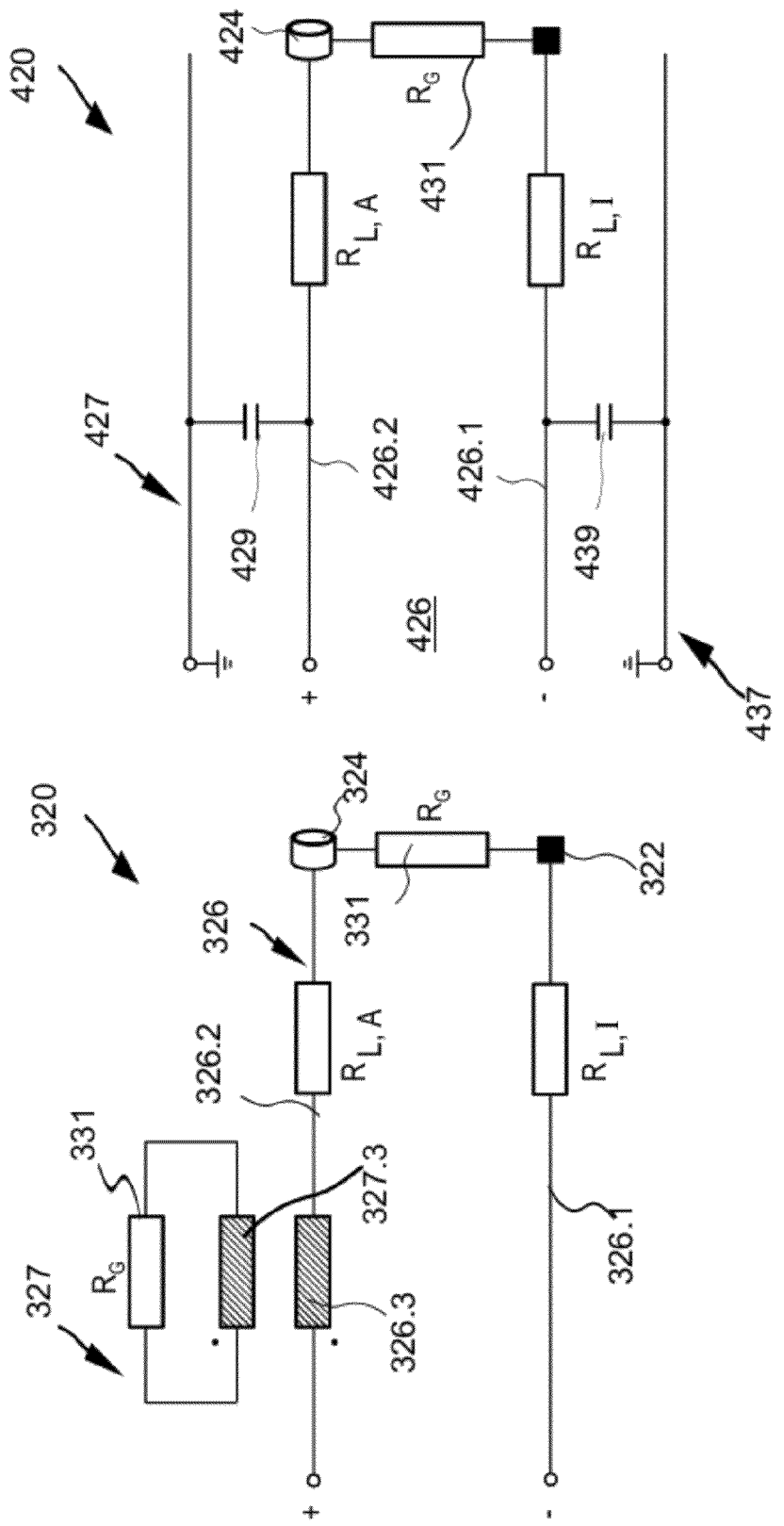
FIG. 3 an equivalent circuit diagram of an embodiment of an electrode lead, in which one or more additional leads each having an electrode pole on its ends is guided parallel to the wires of an outside conductor coil.
FIG. 4 shows an equivalent circuit diagram of an embodiment of an electrode lead, in which a capacitive coupling of two additional leads to the functional leads is implemented.

FIG. 3 shows an equivalent circuit diagram of another embodiment of an electrode lead 320 in the implanted state in which one or more preferably helical additional leads 327 are guided parallel to the conductors of an outer conductor coil 326.2, said coiled additional leads having at their ends one ring-shaped electrode pole each (not shown). The coiled embodiment is especially preferred in the area between 326.3 and 327.3.

A functional lead 326 has an internal conductor 326.1 and an external conductor 326.2. The internal conductor 326.1 is connected distally to a tip electrode pole 322. The external conductor 326.2 is connected to a ring electrode pole 324. Both electrode poles 322 and 324 are connected by bodily tissue represented by an ohmic tissue resistance 331.

An additional lead 327 is inductively coupled to the external conductor 326.2. The energy absorbed by the additional lead 327 via the inductive coupling is dissipated by a ring-shaped electrode pole (not shown) into the bodily tissue 331. The capacitive coupling, which is virtually always present, is not discussed further here. The electrode poles are represented in FIG. 3, so that the shortest path for the current travels over the diverter poles, whereas in FIG. 2 the circuit is closed across Rg and the remote ball. Alternatively, just one diverter pole may also be present, and then the circuit is closed via a capacitive coupling. Ground need not be implemented technically either and instead may be implemented via the potential of the remote ball. The remote ball is defined by a potential in the infinite, such that electrical fields decay rapidly.

The electrode lead 320 has the same advantages as those already discussed in conjunction with the description of electrode lead 220 of FIG. 2.

FIG. 4 shows an equivalent circuit diagram of another embodiment of an electrode lead 420, implementing a capacitive coupling of two additional leads to the functional leads.

A functional lead 426 has an internal conductor 426.1 and an external conductor 426.2. The internal conductor 426.1 is connected distally to a tip electrode pole 422. The external conductor 426.2 is connected to a ring electrode pole 424. Both electrode poles 422 and 424 are connected via bodily tissue, which is represented by an ohmic tissue resistance 431.

In this embodiment, two additional leads 427 and 437 are present. The first additional lead 427 is capacitively coupled to the external conductor 426.2. The second additional lead 437 is capacitively coupled to the internal conductor 426.1.

The electrode lead 420 has the same advantages as those explained in conjunction with the description of the electrode lead 220 of FIG. 2.

FIG. 5 shows a schematic longitudinal sectional view of an electrode lead 520, in which a galvanic coupling is implemented between a functional lead and an additional lead via loop contacts.

The electrode lead 520 contains a functional lead 526 in a sheathing 533, said functional lead comprising an internal conductor 526.1 wound in the form of a coil and an external conductor 526.2, likewise wound in the form of a coil having a larger radius. The external conductor is provided with insulation 526.4, while the internal conductor is uninsulated in the longitudinal section represented here. The external conductor 526.2 is co-radially wound with an additional lead 527 with respect to a central axis A of the cylindrical electrode lead 520. The additional lead is uninsulated in the longitudinal section represented here. At its outer surfaces, the internal conductor is in contact with the internal surfaces of the external conductor 526.2 and of the additional lead 527. In this way, a galvanic coupling in the form of a loop contact is formed at the shared contacting surfaces of the uninsulated internal conductor 526.1 and of the uninsulated additional lead 527. The internal conductor may thus move toward the additional lead without losing the galvanic contact.

The additional lead 527 is thus insulated from the tissue by the sheathing 533 but not with respect to the functional lead 526, which is used for therapeutic or diagnostic purposes. In other words, there may be galvanic contact distributed over the length of the conductor. Nevertheless, in the case of the distributed loop contact implemented here, the functional lead 526 and its additional lead 527 are mechanically movable in relation to one another.

Figure 6:
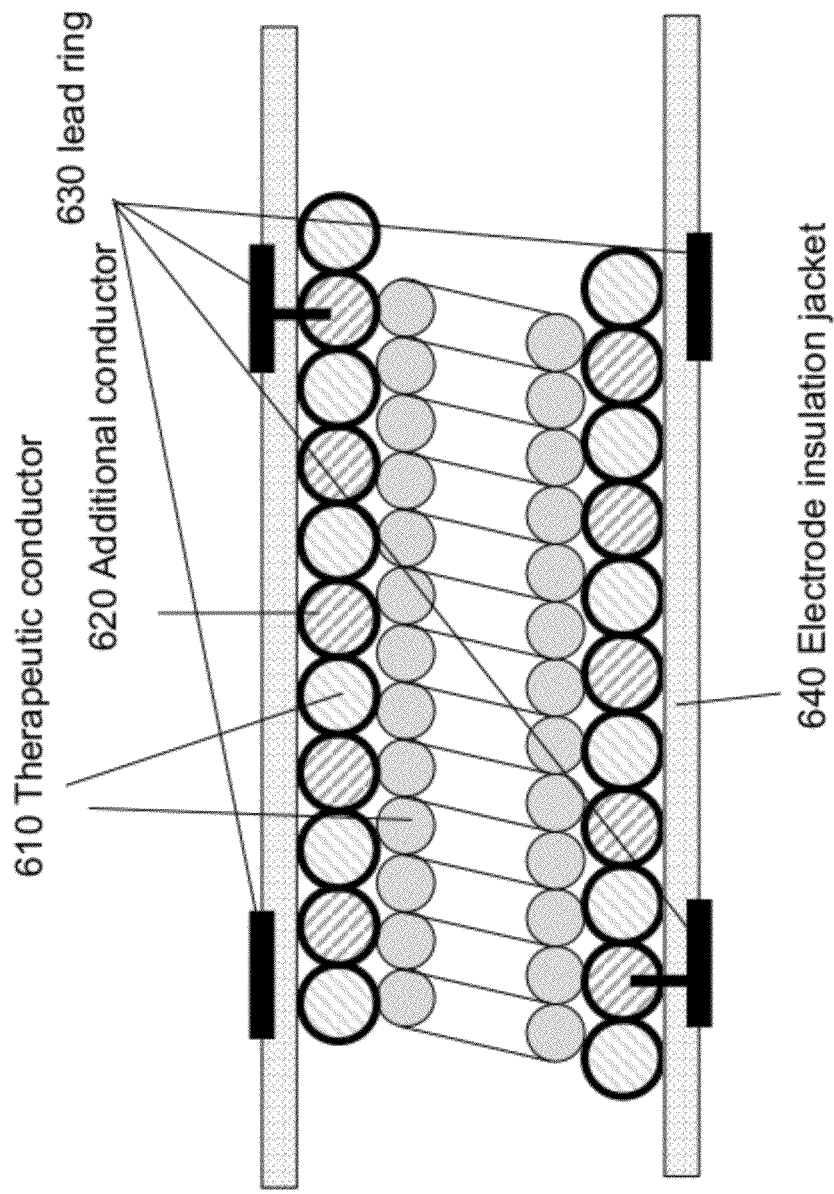
FIG. 6 shows a longitudinal sectional view of an electrode lead having dissipater rings.

FIG. 6 shows a longitudinal sectional view of an electrode lead having leads 630, which have electrical contact with the additional lead 620 and partially protrude out of the electrode insulation jacket 640. The therapeutic conductor 610 is also shown here.

Figure 7:
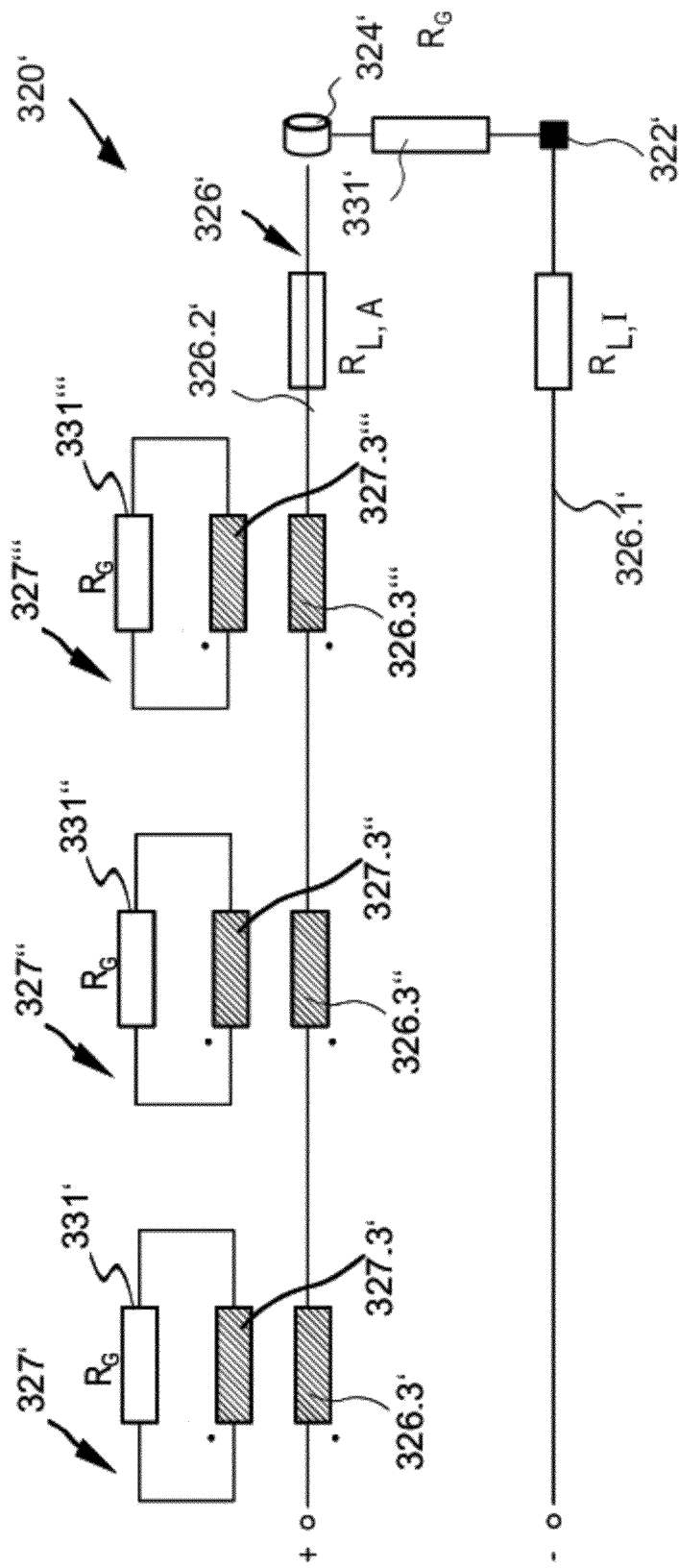
FIG. 7 shows a schematic diagram of another embodiment of an electrode lead in which one or more additional leads is guided in parallel to the conductors of an outside conductor coil.

FIG. 7 shows an equivalent circuit diagram of another embodiment of an electrode lead 320' in the implanted state like that in FIG. 3, but FIG. 7 shows a group of coiled additional leads 327', 327'', 327''' with two diverter poles, which are installed repeatedly at certain intervals along the conductor. However, the additional leads per se are not connected in series here. Apart from the prime notation ['], which is intended for differentiation, the reference notation denotes the same elements as in FIG. 3.

It should be pointed out that in all the embodiments described above, the functional lead or the additional lead may optionally have a higher conductivity than the other of these two leads.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device, comprising
an electrode lead with a central axis compromising
a shared insulating sheathing;
a functional lead connected to a functional electrode pole, wherein said functional lead comprises an internal conductor and an external conductor, and is configured to dispense therapeutic signals or to detect diagnostic signals; and,
an additional lead coupled to the functional lead,
wherein said additional lead comprises at least one second electrical conductor,
wherein said additional lead is guided with the functional lead in said shared insulating sheathing, such that a coupling is formed between the functional lead and the additional lead to input electromagnetic radiofrequency waves guided in the functional lead at least partially into the additional lead;
wherein said additional lead is inductively and capacitively coupled to said external conductor of said functional lead;
wherein said inductive coupling between said additional lead and said external conductor comprises a helical winding of said external conductor and said additional lead; and,
wherein said capacitive coupling between said additional lead and said external conductor comprises said external conductor and said additional lead wound co-radially side by side with respect to said central axis of said electrode lead, and wherein said external conductor is electrically insulated from said additional lead.

2. The medical device according to claim 1, wherein the functional lead and the additional lead are coupled by inductive coupling.

3. The medical device according to claim 1, wherein the functional lead and the additional lead are coupled by capacitive coupling.

4. The medical device according to claim 1, wherein the functional lead and the additional lead are coupled by ohmic coupling.

5. The medical device according to claim 1, wherein the at least one second electrical conductor comprises a plurality of second electrical conductors, such that the functional lead is coupled to the plurality of second electrical conductors over a longitudinal extent between a proximal end of the functional lead and the functional electrode pole.

6. The medical device according to claim 5, wherein at least two of the plurality of second electrical conductors are coupled to one another in series.

7. The medical device according to claim 5, wherein at least two of the plurality of second electrical conductors are coupled to one another in parallel.

8. The medical device according to claim 1, wherein the additional lead is additionally coupled to the functional electrode pole by an additional coupling.

9. The medical device according to claim 1, further comprising a second electrode pole wherein the additional lead is connected to the second electrode pole, which is different from the functional electrode pole.

10. The medical device according to claim 9, wherein the second electrode pole comprises a dielectric layer that covers said second electrode pole.

11. The medical device according to claim 1, wherein the additional lead comprises a hollow coil that surrounds the internal conductor of the functional lead.

12. The medical device according to claim 11, wherein the internal conductor of the functional lead is coupled to the additional lead by at least one loop contact.

13. The medical device according to claim 1, wherein the additional lead comprises an internal conductor, and wherein the additional lead and the external conductor of the functional lead are wound in a helical form cylindrically around the internal conductor of the additional lead.

14. The medical device according to claim 1, wherein the external conductor of the functional lead is wound in a coil around the additional lead and the internal conductor of the functional lead, such that the internal conductor and the additional lead are each guided in the form of a hollow coil cylindrically.

15. The medical device according to claim 1, wherein said internal conductor of said functional lead is wound in the form of a coil, and wherein said external conductor is wound in the form of a coil having a larger radius than said internal conductor.

16. The medical device according to claim 1, wherein said external conductor and said additional lead are wound in the same direction.

* * * * *